United States Patent [19]

Hansen, deceased

[11] Plant 5,173

[45] Jan. 10, 1984

[54] ALMOND×PEACH HYBRID ROOTSTOCK TREE

[75] Inventor: Carl J. Hansen, deceased, late of Citrus Heights, Calif., by Betty C. Hansen, heir

[73] Assignee: The Regents of the University of California, Berkeley, Calif.

[21] Appl. No.: 408,715

[22] Filed: Aug. 16, 1982

[51] Int. Cl.[3] ..... A01H 5/03

[52] U.S. Cl. ..... Plt./30

[58] Field of Search ..... Plt./30, 42

*Primary Examiner*—Robert E. Bagwill

*Attorney, Agent, or Firm*—Roger B. Webster

[57] ABSTRACT

An almond×peach hybrid rootstock tree which is large, half-hardy, vigorous, upright to vase-shaped, with appearance of the peach but larger and more vigorous; the trunk is of medium size with vertical fissures and striations, gray-brown, with old bark brown with whitish overcolor; new shoots, together with young leaves, are a prominent red color; leaves are large, thin, smooth, and dark green with a crenate-serrate margin, medium length petiole, and uniform glands; blooms from medium size, half-hardy, plump, pubescent buds, mature buds are green and distinctly reddish on exposed parts; the flowers are large and showy, with large petals pink to red in bud, and rose color when flowers are fully open; the tree is a productive bearer of ovate, white-fleshed fruit (not useful to the clone) having a very hard, reddish-brown, peach-like stone with large ridges and grooves; and the tree root system is adventitious and deep-rooting with a large number of prominent, vigorous, thick, smooth, straight but somewhat tapering, main roots which radiate outwardly and downwardly from the base of the trunk.

3 Drawing Figures

BACKGROUND OF THE VARIETY

Field of the Invention

The inventor, Carl J. Hansen, in the conduct of an extensive plant breeding program, originated a substantial number of new and distinct plant varieties, and which included the present almond×peach hybrid rootstock tree. Such plant breeding program was undertaken by inventor, Carl J. Hansen, in the research and experimental plant nursery and orchards of the Department of Pomology at the University of California, Davis, Yolo County, Calif.

Classification of the Variety

The present variety of rootstock tree is embraced by Subclass 30, Plants, of the U.S. Patent Office Manual of Classification.

Existing Varieties

Among existing plant varieties known to inventor, Carl J. Hansen, and mentioned herein for the purpose of reference or comparison, are the following:

Almond Tree ("Almond B"), an unpatented chance seedling selected from a commercial orchard located near Ballico, Merced County, Calif.; Peach Tree ("Peach 1-8-2"), an unpatented selection of the Department of Pomology, University of California, Davis, Calif.;

Almond×Peach rootstock tree ("Hansen 2168"), a selection of the Department of Pomology, University of California, Davis, Calif., and the subject of co-pending U.S. plant patent application Ser. No. 408,612, filed Aug. 16, 1982; Almond Tree ("Nonpareil"), unpatented; Plum Tree ("Marianna"), unpatented; and Peach Tree ("Lovell"), unpatented.

ORIGIN OF THE VARIETY

The present variety of almond×peach hybrid rootstock tree was originated by inventor, Carl J. Hansen, in the aforesaid research and experimental plant nursery and orchards, as a cross—by hand pollination—between "Almond B" and "Peach 1-8-2", and was a selection from a seedling population of said cross; the selection having been made upon the ascertainment—under careful and continuing observation—that the present $F_1$ clone bore certain desirable characteristics for use as a rootstock.

ASEXUAL REPRODUCTION OF THE VARIETY

Subsequent to its origination and selection, as above, the present almond×peach hybrid rootstock tree was successfully asexually reproduced by inventor, Carl J. Hansen, in the aforesaid research and experimental plant nursery and orchards; the reproductions having been accomplished from hardwood cuttings, and, in maturity, in certain test plots in the aforesaid experimental orchards, said reproductions ran true, in all respects, to the original tree of the present variety. Vegetative reproduction of the variety has also been successfully accomplished from softwood cuttings under mist, and by budding.

SUMMARY OF THE VARIETY

The present variety of almond×peach hybrid rootstock tree is large, half-hardy, vigorous, upright to vase-shaped, with appearance of the peach but larger and more vigorous; the trunk is of medium size with vertical fissures and striations, gray-brown, with old bark brown with whitish overcolor; new shoots, together with young leaves, are a prominent red color; leaves are large, thin, smooth, and dark green with a crenate-serrate margin, medium length petiole, and uniform glands; blooms from medium size, half-hardy, plump, pubescent buds, mature buds are green and distinctly reddish on exposed parts; the flowers are large and showy, with large petals pink to red in bud, and rose color when flowers are fully open; the tree is a productive bearer of ovate, white-fleshed fruit (not useful to the clone) having a very hard, reddish-brown, peach-like stone with large ridges and grooves; and the tree root system is adventitious and deep-rooting with a large number of prominent, vigorous, thick, smooth, straight but somewhat tapering, main roots which radiate outwardly and downwardly from the base of the trunk.

Further, the present variety of almond×peach hybrid rootstock tree—in addition to high vigor and which is greater than that of rootstocks commonly used for almonds and stone fruit—is immune to root-knot nematodes *Meloidygyne incognita acrita* and *M. javanica;* is more tolerant to iron chlorosis than peach rootstocks; and, although not highly resistant to *Phytopthora syringae* and "wet feet" conditions associated with crown rot problems, is somewhat more tolerant than other hybrids tested, and about at the level of peach rootstocks (such as "Lovell"), but more tolerant than almond.

Still further, the present variety of almond×peach hybrid rootstock tree, because of its extensive and deep root system, provides excellent tree anchorage, and is more tolerant to drought and marginal growing conditions than peach rootstock as well as the Marianna plum, but probably not almond. The tree anchorage is better than commonly used rootstocks, peach and the Marianna plum.

Additionally, the present variety of almond×peach hybrid rootstock tree is readily propagated from hardwood cuttings, although the rooting percentages (65%–85%) have been somewhat less than the "Hansen 2168".

In additional comparison to the "Hansen 2168", the present variety has a greater tendency to produce red coloration of the flowers and of the young leaves and shoots in the Spring, in addition to more red on dormant shoots.

In still an additional comparison to the "Hansen 2168", the root system of the present variety has more small, fine roots associated with the main roots.

In still an additional comparison to the "Hansen 2168", the present variety, while having general resemblance, is slightly less vigorous, yet somewhat more tolerant to crown rot problems associated with *Phytopthora syringae.*

BRIEF DESCRIPTION OF THE DRAWING

The drawing is an illustration, by photographic reproduction in color, and in one view, of a tree of the variety; in another view, flowers of the variety; and, in a still further view, the root system out of ground and cut from the tree.

DESCRIPTION OF THE VARIETY

The botanical details of the present new and distinct variety of almond×peach hybrid rootstock tree—with color definitions in common color terms—are as follows:

Tree:

*Size.*—Large.

*Vigor.*—Vigorous.

*Form.*—Upright to vase-shaped. Bearing habit similar to peach in that flowers are borne on lateral shoots. Vegetative shoots are very vigorous.

*Hardiness.*—Half-hardy.

*Productivity.*—Tree bears large number of fruit which are not useful to the clone.

*Use.*—Rootstock, primarily for almond and peach, but plum and prune varieties are compatible. Not compatible to apricot.

*Root system.*—Deep rooting. Adventitious with a large number of prominent, vigorous, thick, smooth, straight but somewhat tapering main roots which radiate outwardly and downwardly from the base of the trunk providing excellent tree anchorage. Roots develop readily on hardwood cuttings.

Trunk:

*Size.*—Medium.

*Color.*—Grayish-brown with vertical fissures or striations. Old bark: Brown with whitish overcolor.

Branches:

*Shoots.*—Color: Green, with distinct reddish color on exposed parts. New shoots and young leaves have prominent red color, and which is more conspicuous than on "Hansen 2168."

*Lenticels.*—Numerous. Horizontal. Average 1/10" to ¼" in length.

Leaves:

*Size.*—Large (vigorous shoot leaves). Average length — 73 mm. (range 65 to 85 mm.). Average width — 28 mm. (range 25 to 30 mm.). Ratio of width to length — 1:3.8.

*Thickness.*—Thin.

*Texture.*—Smooth.

*Color.*—Dark green.

*Margin.*—Crenate-serrate.

*Petiole.*—Medium length. Longer than peach, but shorter than almond. In relation to length of blade, intermediate between peach and almond. Average length — 20 mm. Ratio of petiole to blade — 1:3.7.

*Glands.*—Number — 0 to 2. Mostly uniform.

Flower buds:

*Size.*—Medium.

*Hardiness.*—Half-hardy.

*Form.*—Plump.

*Pubescence.*—Pubescent.

Flowers:

*Blooming period.*—Mid-February. About with or slightly earlier than the Nonpareil almond.

*Size.*—Large. Average — 40–45 mm. in diameter when fully open. Showy.

*Peduncle.*—Glabrous. Average length — 3 mm.

*Calyx.*—Green overlaid with red.

*Sepals.*—Green to reddish. Glabrous at base, becoming pubescent at lobes and margins.

*Petals.*—Large. Pink to red in bud, and remaining rose color when open. Prominent red at base of petal; red gradually fades, but remains distinctly more reddish than "Hansen 2168". Pronounced emarginate notch at apical end of petal. Average size — 15×18 mm.

*Stamens.*—Long. Average size — 10 mm. Predominantly red.

*Anthers.*—Yellow.

*Pistils.*—Straight. Very pubescent. Tend to become reddish. Few undeveloped.

Fruit:

*Season of maturity.*—Ripens in August.

*Bearing.*—Productive but non-useful. Borne on long shoots similar to peach.

*Form.*—Tends to be ovate and intermediate in structural characteristics between peach and almond.

*Flesh.*—White. Becomes somewhat soft and develops a suture which tends to split at maturity without separating completely from stone.

*Pubescence.*—Skin highly pubescent.

*Flavor.*—Astringent.

Stone:

*Form.*—Peach-like in appearance.

*Ridges and grooves.*—Large. Very hard.

*Color.*—Reddish brown.

*Kernel.*—Inedible.

Resistance to insects and diseases: Immune to root-knot nematodes *Meloidygyne incognita acrita* and *M. javanica.* Some tolerance to iron chlorosis. Some tolerance to *Phytopthora syringae.*

The herein described almond×peach hybrid rootstock tree may vary in slight detail due to climatic and soil conditions under which the variety may be grown; the present description being of the variety as grown in the Central Valley of California.

I claim:

1. A new and distinct variety of almond×peach hybrid rootstock tree, substantially as illustrated and described, particularly characterized by a relatively high percentage of successful reproductions from hardwood cuttings, by a deep rooting, adventitious root system which provides excellent anchorage, by immunity to root-knot nematode infections, *Meloidygyne incognita acrita* and *M. javanica,* and by a tree generally resembling the "Hansen 2168" but slightly less vigorous, roots from cuttings at a somewhat less rooting percentage, has more red color of the flowers and of the young leaves and shoots in the Spring, and has more small, fine roots associated with the main roots of the root system.

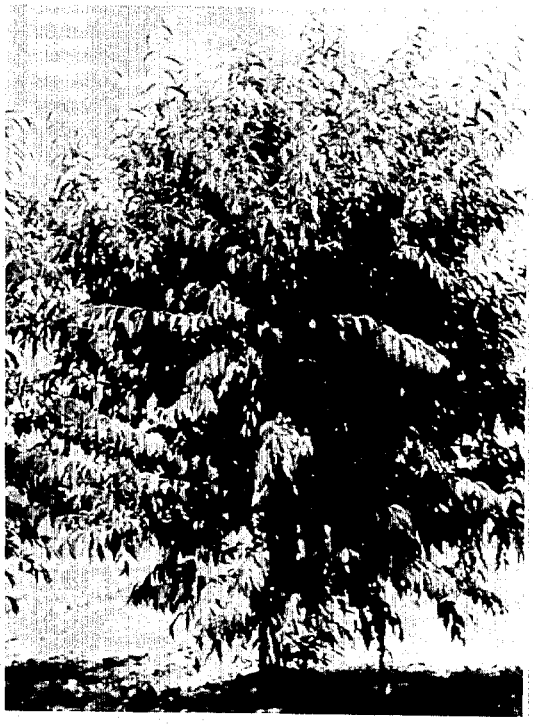
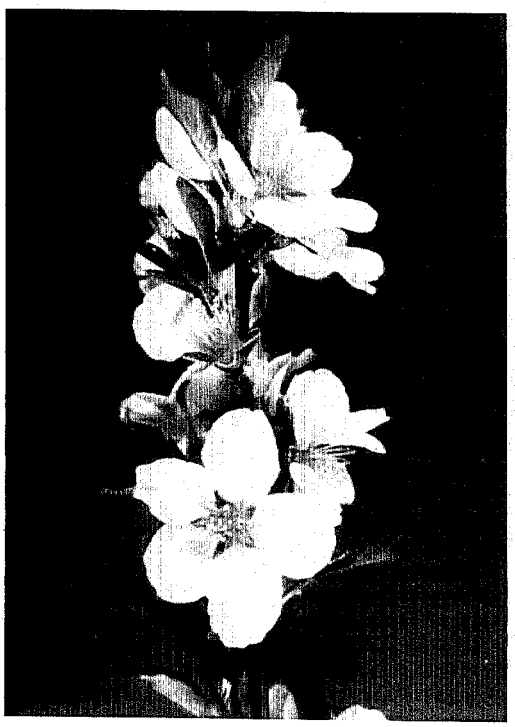
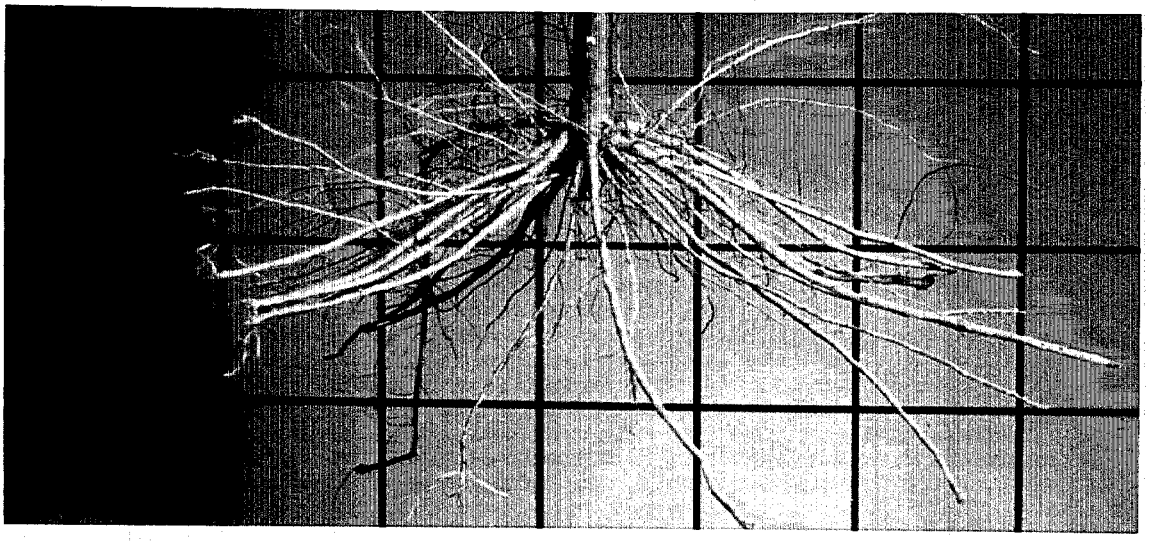

* * * * *